(12) United States Patent
Harrold et al.

(10) Patent No.: US 8,521,264 B2
(45) Date of Patent: Aug. 27, 2013

(54) METHOD FOR MONITORING ICG/ECG SIGNALS

(75) Inventors: Lewis Norman Harrold, Georgetown, MA (US); Anthony Ralph DiCiaccio, Peabody, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 13/600,707

(22) Filed: Aug. 31, 2012

(65) Prior Publication Data

US 2012/0323106 A1 Dec. 20, 2012

Related U.S. Application Data

(62) Division of application No. 12/489,156, filed on Jun. 22, 2009, now abandoned.

(51) Int. Cl.
*A61B 5/04* (2006.01)
*A61B 5/05* (2006.01)

(52) U.S. Cl.
USPC ........... 600/509; 600/372; 600/382; 600/393; 600/547

(58) Field of Classification Search
USPC ................ 600/372, 382, 386, 388, 391–397, 600/506, 509, 547
See application file for complete search history.

(56) References Cited

U.S. PATENT DOCUMENTS

| | | | |
|---|---|---|---|
| 5,036,869 A * | 8/1991 | Inahara | 600/481 |
| 5,400,796 A * | 3/1995 | Wecke | 600/518 |
| 6,102,869 A | 8/2000 | Meier et al. | |
| 6,327,487 B1 * | 12/2001 | Stratbucker | 600/382 |
| 6,496,732 B1 | 12/2002 | Wallace | |
| 6,511,438 B2 | 1/2003 | Bernstein et al. | |
| 7,079,977 B2 * | 7/2006 | Osorio et al. | 702/176 |
| 7,197,357 B2 | 3/2007 | Istvan et al. | |
| 7,214,189 B2 | 5/2007 | Zdeblick | |
| 7,272,428 B2 | 9/2007 | Hopman et al. | |
| 7,277,751 B2 | 10/2007 | Dupelle et al. | |

(Continued)

FOREIGN PATENT DOCUMENTS

| | | |
|---|---|---|
| WO | 2005094498 | 10/2005 |
| WO | 2006041785 | 4/2006 |

OTHER PUBLICATIONS

Bernstein, et al., Stroke volume equation for impedance cardiography, Med. Biol. Eng. Comput., 2005, pp. 443-450, vol. 43, abstract attached.

(Continued)

*Primary Examiner* — Linda Dvorak
*Assistant Examiner* — Brian M Antiskay
(74) *Attorney, Agent, or Firm* — Driggs, Hogg, Daugherty & Del Zoppo Co., LPA

(57) ABSTRACT

An ICG/ECG electrode includes a first electrode and a second electrode, wherein at least one of the first or second electrode senses both an ICG signal and an ECG voltage signal. A physiologic parameter monitoring apparatus includes a set of electrodes, including an electrode for sensing both an ICG voltage signal and an ECG voltage signal corresponding to a patient. The apparatus further includes an ICG monitor for processing the ICG voltage signal sensed by the electrode and an ECG monitor for processing the ECG voltage signal sensed by the same electrode.

20 Claims, 3 Drawing Sheets

(56) References Cited

U.S. PATENT DOCUMENTS

| | | | |
|---|---|---|---|
| 2005/0124901 A1* | 6/2005 | Misczynski et al. | 600/509 |
| 2005/0215918 A1 | 9/2005 | Frantz et al. | |
| 2006/0111641 A1* | 5/2006 | Manera et al. | 600/513 |
| 2006/0155354 A1 | 7/2006 | Heath | |
| 2006/0178706 A1 | 8/2006 | Lisogurski et al. | |
| 2007/0219454 A1 | 9/2007 | Guzzetta et al. | |
| 2008/0058652 A1* | 3/2008 | Payne | 600/488 |
| 2010/0324404 A1 | 12/2010 | Harrold et al. | |

OTHER PUBLICATIONS

Summers, et al., Bench to Bedside: Electrophysiologic and Clinical Principles of Noninvasive Hemodynamic Monitoring Using Impedance Cardiography, ACAD Emerg Med, Jun. 2003, pp. 669-680, vol. 10, No. 6.

* cited by examiner

METHOD FOR MONITORING ICG/ECG SIGNALS

CROSS-REFERENCE TO RELATED APPLICATION

This application is a divisional of U.S. application Ser. No. 12/489,156, filed Jun. 22, 2009.

TECHNICAL FIELD

The following generally relates to a physiologic parameter monitoring apparatus and is described with particular application to impedance cardiography (ICG)/electrocardiography (ECG) monitoring utilizing at least one shared ICG/ECG electrode.

BACKGROUND

Impedance cardiography (ICG) is used to derive various cardiac parameters based on the impedance of blood flowing through the heart. With ICG, historically four pairs of electrodes are attached to the patient, two pairs at opposing regions about the neck and two pairs at opposing regions about the front lower chest. One electrode of each pair is used to inject a pre-determined electrical current, which travels through a low resistance path in the body such as blood flowing from the heart. The other electrode of each pair detects a signal indicative of a change in impedance (thoracic electric bio-impedance) of the blood flowing from the heart during each heart cycle based on the change in impedance from the change in voltage induced by the injected electrical current.

Electrocardiography (ECG) is used to sense and record electrical activity of the heart. For a commonly used Wilson three-lead ECG, two electrodes are attached to opposing shoulder regions and a third electrode is attached to the front lower chest area. The different electrodes sense electrical activity of the heart during each heart cycle. Historically, difference signals, corresponding to differences between voltage measurements for pairs of electrodes, are generated and graphically presented as waves (e.g., on a display or paper) and provide information about the heart. This information can be used to identify electrical rhythms of the heart, including abnormal electrical rhythms, heart muscle damage, and/or other information.

When the above noted ICG and three-lead ECG configurations are used in conjunction, a relatively large number of electrodes (e.g., seven, or four electrode pairs for ICG and three separate and distinct electrodes for ECG) are affixed to the patient. With five and twelve lead ECG configurations, even more electrodes are attached to the patient. Moreover, cables are run from each electrode to the ICG and ECG monitoring apparatuses.

SUMMARY

Aspects of the application address the above matters, and others.

In one aspect, an ICG/ECG electrode includes a first electrode contact and a second electrode contact. At least one of the first or second electrode contacts senses both an ICG voltage signal and an ECG voltage signal.

In another aspect, a physiologic parameter monitoring apparatus includes a set of electrodes, including an electrode for sensing both an ICG voltage signal and an ECG voltage signal corresponding to a patient. The apparatus further includes an ICG monitor for processing the ICG voltage signal sensed by the electrode and an ECG monitor for processing the ECG voltage signal sensed by the electrode.

In another aspect, a method includes supplying a ICG current signal to one electrode of a pair of electrodes of at least one of no more than three sets of pairs of electrodes affixed to a patient about the heart of the patient, sensing an ICG voltage signal by the other electrode of the pair of electrodes, and generating a cardiac parameter based on the ICG current signal and the ICG voltage signal.

In another aspect, a method includes supplying a first ICG signal to one electrode of a pair of electrodes affixed to a patient about the heart of the patient. The method further includes sensing a second ICG signal by the other electrode of the pair of electrodes and generating a cardiac parameter based on the second ICG signal. The method further includes sensing a signal indicative of an electrical activity of the heart of the patient by the same electrode that senses the second ICG signal and generating an ECG signal based on the sensed signal indicative of an electrical activity of the heart. The method further includes presenting the cardiac parameter and the ECG signal indicative of heart electrical activity.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
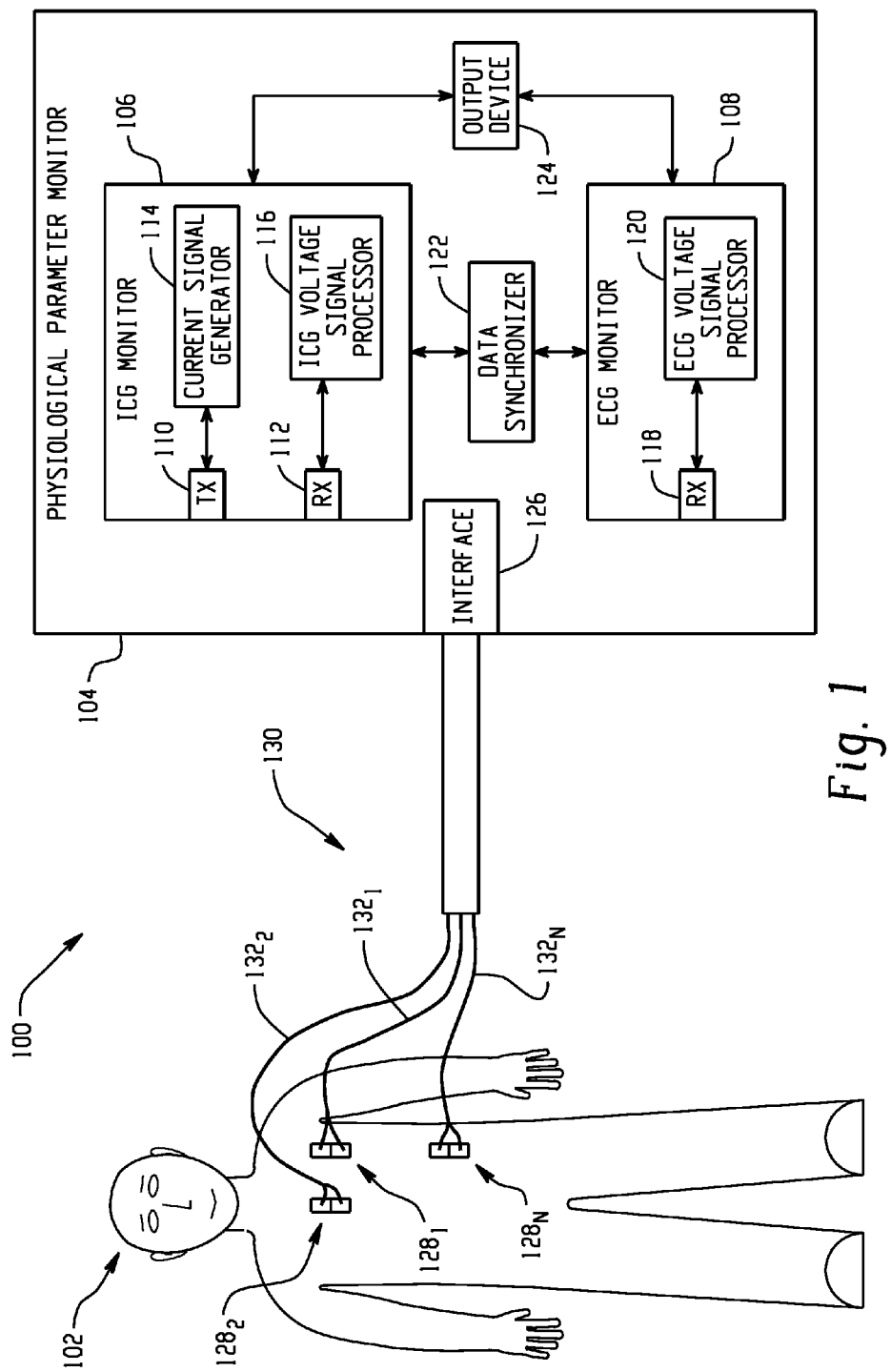
FIG. 1 illustrates an example physiologic monitoring apparatus.

FIG. 1 illustrates a physiologic monitoring apparatus 100 in connection with a patient 102. The illustrated physiologic monitoring apparatus 100 includes a physiologic parameter monitor 104, with an impedance cardiography (ICG) monitor 106 and an (electrocardiography) ECG monitor 108, and is configured for concurrent and individual ICG/ECG monitoring.

The ICG monitor 106 includes a current transmitter 110 and a voltage receiver 112. The current transmitter 110 is configured to supply a predetermined ICG electrical current signal to be applied to the patient 102. The voltage receiver 112 is configured to receive a sensed voltage signal. The voltage signal is used to determine a bio-impedance of blood flowing from the heart of the patient 102 due to the applied current signal from the ICG transmitter 110.

A signal generator 114 generates the ICG current signal. In the illustrated embodiment, the signal generator 114 generates a biphasic electrical current signal in a range of about one (1) to four (4) milliamps (mA). The biphasic nature of the current signal provides for a current with a substantially zero time average (or essentially no DC component), which can mitigate electrode polarization, which may affect ECG voltage signal reception and/or processing. The frequency of the generated current signal is in a range of about seventy thousand Hertz (70 k Hz) to about one hundred and fifty thousand Hz (150 k Hz), which allows for passing the current signal through the skin.

An ICG voltage signal processor 116 processes the received sensed voltage signal. The ICG voltage signal processor 116 determines various information based on the sensed voltage signal from the sensing electrodes. Example of such information includes, but is not limited to, cardiac output, heart rate, and/or other cardiac information.

The ECG monitor 108 includes a receiver 118 configured to receive a sensed voltage signal indicative of the electrical activity of the heart. An ECG signal processor 120 processes the received sensed electrical signal.

A data synchronizer 122 synchronizes data acquisition of the bio-impedance and heart electrical activity signals. Synchronization can be time synchronized through a crystal controlled or other timing device. In one instance, the signals are synchronized through a common clock. In another instance, the signals are sampled based on separate clocks, and the data synchronizer 122 synchronizes the data by synchronizing on the two clocks. The timing of the signals can also be used to facilitate discriminating between the signals and noise.

An output device 124 allows for presenting the ICG and/or ECG signals on a display, paper and/or other human readable medium.

An interface 126 is configured to route the transmitted ICG electrical current from the physiologic parameter monitor 104 to the patient 102 and/or the sensed signals from the patient 102 respectively to the ICG and ECG monitors 106 and 108.

A plurality of sets of electrodes $128_1$, $128_2$ and $128_N$ (collectively referred to as sets of electrodes 128) are affixed to the patient 102. In the illustrated embodiment, N=3 and the sets of electrodes 128 are positioned on the patient 102 to facilitate applying the ICG electrical current signal in connection with predetermined anatomy (e.g., the pulmonary artery and aorta) and sensing signals with respect to such anatomy. Note that the illustrated positioning of the electrode pairs 128 is similar to three-lead ECG electrode positioning. As described in greater detail below, at least one electrode of at least one of the sets of electrodes 128 is shared for both ICG and ECG monitoring. In one instance, sharing an electrode contact as such allows for reducing the overall number of electrodes affixed to the patient 102 relative to a configuration in which separate electrodes are used for ICG and ECG monitoring.

A communications channel 130 such as a cable or the like includes respective sets of connectors $132_1$, $132_2$ and $132_N$ (collectively referred to as connectors 132) that connect to and couple the plurality of sets of pairs of electrodes $128_1$, $128_2$ and $128_N$ and the physiologic parameter monitor 104.

Figure 2:
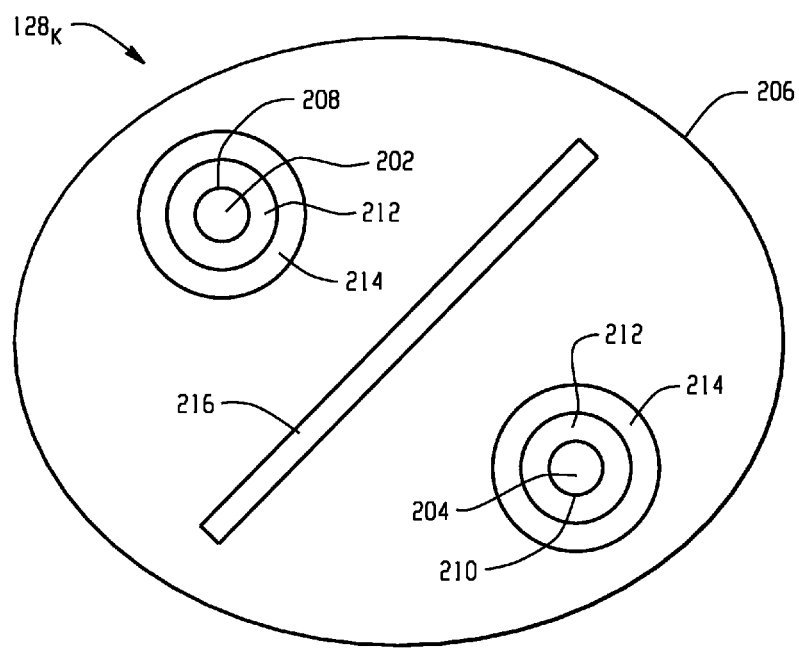
FIG. 2 illustrates an example shared ICG/ECG electrode.

FIG. 2 illustrates an example set of electrodes $128_K$. The set of electrodes $128_K$ includes a pair of electrodes, including first and second electrodes or electrode contacts 202 and 204, affixed to a substrate 206 such as a patch or the like.

The illustrated electrodes 202 and 204 are circular in shape. In other embodiment, the electrodes 202 and 204 are otherwise shaped, such as polygonally shaped, elliptically shaped, or otherwise shaped. The electrodes 202 and 204 include a conductive material such as silver-chloride material and/or other conductive material.

The first and second electrodes 202 or 204 are disposed in respective separate wells 208 and 210. The first and second electrodes 202 or 204 are successively surrounded by first and second barriers 212 and 214. The illustrated barriers 212 and 214 are "O" or donut shaped and form concentric rings around the electrodes 202 or 204.

The first barrier 212 includes a non-adhesive material and the second barrier 214 includes an adhesive material. In the illustrated embodiment, the adhesive material is a gel and mitigates cross-coupling between the supplied ICG current and the sensed heart electrical activity signal, which may facilitate mitigating corruption of the sensed heart electrical activity by the ICG signal. In other embodiments, the adhesive material includes another electrically insulating material.

A third barrier 216 is linearly or line shaped and disposed along the substrate 206 between the first and second electrodes 202 or 204. In another embodiment, the third barrier 216 is irregular or otherwise shaped. Similar to the second barrier 214, the third 216 includes an adhesive material, and the adhesive material can be in the form of a gel and also mitigate cross-coupling between the supplied ICG current signal and the sensed signals.

One of the first or second electrodes 202 or 204 is used for supplying the ICG electrical current signal. The other of the electrodes 202 or 204 is used to concurrently or individually sense (by the ICG monitor 106 and the ECG monitor 108) the bio-impedance and the heart electrical activity voltage signals.

Figure 3:
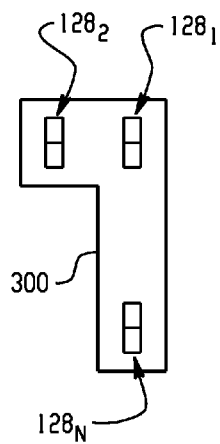
FIG. 3 illustrates an example electrode carrier.
Figure 4:
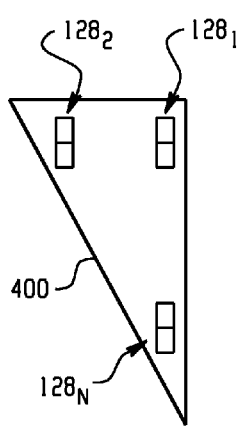
FIG. 4 illustrates another example electrode carrier.
Figure 5:
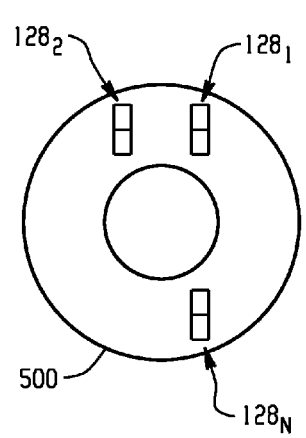
FIG. 5 illustrates another example electrode carrier.

FIGS. 3, 4 and 5 illustrate various non-limiting embodiments in which the sets of electrodes 128 are carried by a carrier.

In FIG. 3, three sets of electrodes 128 are carried by an "L" shaped carrier 300. The "L" shaped carrier 300 removeably affixes to the patient via an adhesive such as the adhesives 214 and 216 of the electrodes 128 described in connection with FIG. 2. In another embodiment, the carrier 300 additionally includes one or more elements for securing the carrier 300 to the patient 102.

Turning to FIG. 4, a carrier 400 is substantially similar to the carrier 300 except that the carrier 400 is triangular shaped.

Likewise, in FIG. 5, a carrier 500 is substantially similar to the carrier 300 except for its shape. As shown in FIG. 5, the carrier 500 is "O" shaped.

Other shapes are also contemplated herein. For example, in another instance, the carrier is configured to conform to the contour of the body.

In one instance, the carriers 300, 400 and 500 are positioned on the patient 102 so that the electrodes 128 are located about the heart of the patient 102 as described herein.

Variations are contemplated.

In another embodiment, the ICG and the ECG monitors 106 and 108 are part of separate physiologic parameter monitoring devices.

In another embodiment, one or both of the ICG and the ECG monitors 106 and 108 are portable units. In such an embodiment, one or both of the ICG and the ECG monitors 106 and 108 are configured to attach to the carriers 300, 400, and/or 500.

In another embodiment, the sets of electrodes 128 include wireless transceivers and communicate with the monitor 104 via the wireless transceivers.

In another embodiment, the individual sets of connectors $132_1$, $132_2$ and $132_N$ are included in separate cables.

In another embodiment, the signal generator 114 generates a signal with an average value that produces a polarization voltage that opposes the polarization voltage of the contacts 202 and 204. Where the electrodes 202 and 204 include a silver-chloride material, such a polarization voltage is in a range from about two hundred and fifty (250) milliVolts (mV) to about three hundred and fifty (350) mV.

Example methods are described.

Figure 6:
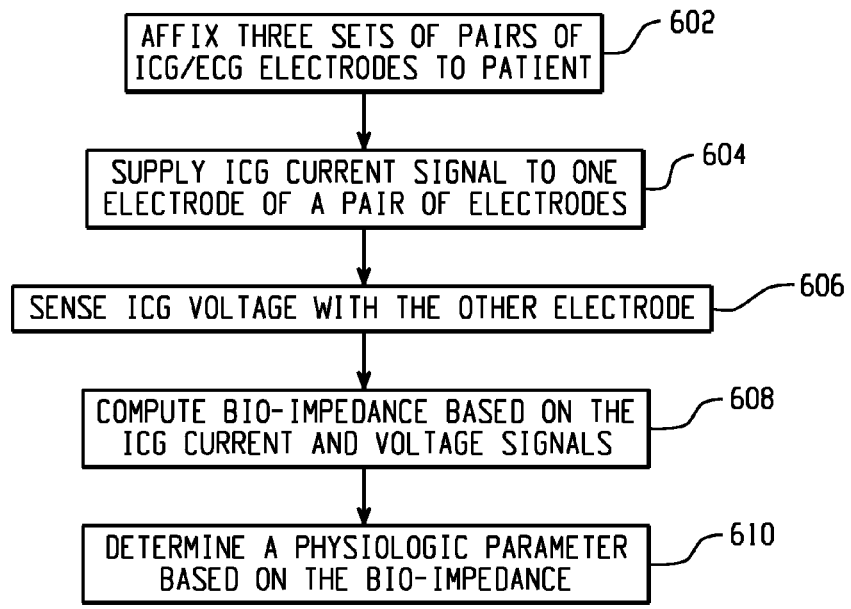
FIG. 6 illustrates an example method.

FIG. 6 illustrates a method for acquiring an ICG electrical voltage signal.

At 602, three sets of pairs of electrodes 128 are affixed to the patient 102 about the heart of the patient 102. As described herein, the sets of electrodes 128 may be individually affixed to the patient 102 or part of the carrier 300, 400, or 500.

At 604, an ICG electrical current signal is supplied to one electrode 202 or 204 of a pairs of electrodes 128. The ICG current signal generally is an electrical alternating current signal that traverses a path of lower resistance such as the blood flowing from the heart such as from the pulmonary artery and/or aorta.

At 606, an ICG voltage signal is sensed by the other electrode 202 or 204 of the pair of electrodes 128.

At 608, a bio-impedance of the blood flowing from the heart is computed based on the sensed ICG voltage signal and the applied ICG current signal. The bio-impedance and hence the sensed signal varies as the heart expands and contracts and blood flow velocity varies.

At 608, the sensed signal is processed to determine at least one cardiac parameter.

Figure 7:
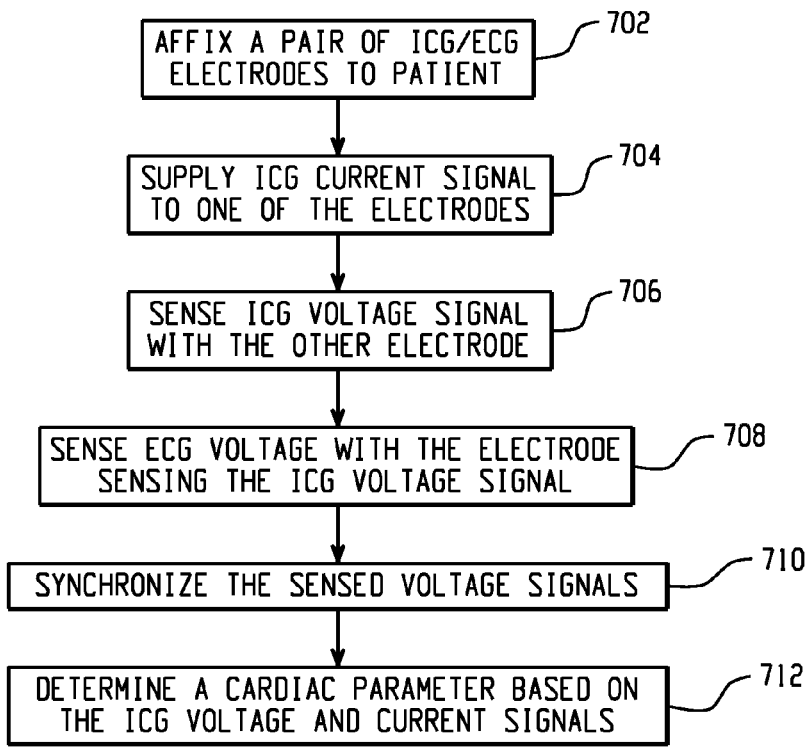
FIG. 7 illustrates another example method.

FIG. 7 illustrates a method for acquiring an ICG and an ECG signal. It is to be appreciated that the ordering of the following acts is provided for explanatory purposes and other ordering is contemplated herein.

At 702, a pair of electrodes 128 is affixed to the patient 102 about the heart of the patient 102 as described herein.

At 704, an ICG electrical current signal is supplied to one electrode 202 or 204 of the pair of electrodes 128.

At 706, an ICG voltage signal is sensed by the other electrode 202 or 204 of the pair of electrodes 128.

At 708, an ECG voltage signal is sensed by the electrode sensing the ICG voltage signal.

At 710, the sensed ICG and ECG voltage signals are time-synchronized.

At 712, a cardiac parameter is determined based on the sensed ICG voltage signal and the applied ICG current signal.

The above may be implemented by way of computer readable instructions, which when executed by a computer processor(s), cause the processor(s) to carry out the acts. The instructions can be stored in a computer readable storage medium associated with or otherwise accessible to the relevant computer.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method of utilizing no more than three ICG/ECG electrode pairs to sense both ICG and heart electrical activity signals, the method comprising: sensing, with a first electrode contact and a second electrode contact of a first pair of the no more than three ICG/ECG electrode pairs, a first ICG signal and a first heart electrical activity signal; sensing, with a first electrode contact and a second electrode contact of a second pair of the no more than three ICG/ECG electrode pairs, a second ICG signal and a second heart electrical activity signal; sensing, with a first electrode contact and a second electrode contact of a third pair of the no more than three ICG/ECG electrode pairs, a third ICG signal and a third heart electrical activity signal; utilizing different clocks to sense the first, second and third ICG signals and the first, second and third heart electrical activity signals; synchronizing the different clocks, thereby time-synchronizing the sensed first, second and third ICG signals with the first, second and third heart electrical activity signals; and determining a cardiac parameter based on the first, second and third ICG signals and an EKG signal based on the first, second and third heart electrical activity signals.

2. The method of claim 1, further comprising:
employing the no more than three ICG/ECG electrode pairs to concurrently sense both ICG and heart electrical activity signals.

3. The method of claim 1, further comprising:
employing the no more than three ICG/ECG electrode pairs to individually sense both ICG and heart electrical activity signals.

4. The method of claim 1, wherein at least one of the no more than three pairs of the three ICG/ECG electrode pairs includes first and second electrode contacts affixed to a substrate with a barrier disposed on the substrate between the first and second electrode contacts and protruding from the substrate, wherein the barrier is physically separated from the first and second electrode contacts by a sub-region of the substrate.

5. The method of claim 1, wherein the no more than three pairs of electrodes are based on the Wilson three-lead ECG configuration.

6. The method of claim 1, further comprising:
processing the first, second and third ICG signals; and
processing the first, second and third heart electrical activity signals.

7. The method of claim 1, further comprising: generating a biphasic ICG electrical current signal; and supplying a current signal to at least one of the contacts of the no more than three ICG/ECG electrode pairs.

8. The method of claim 7, wherein the biphasic ICG electrical current signal has a zero time-average value.

9. The method of claim 8, wherein the biphasic ICG electrical current signal has a polarization value equal to about a polarization of the electrodes.

10. The method of claim 8, wherein the no more than three ICG/ECG electrode pairs is exactly three ICG/ECG electrode pairs.

11. A method of utilizing no more than three ICG/ECG electrode pairs to sense both ICG and heart electrical activity signals, the method comprising: sensing, with a first electrode contact and a second electrode contact of a first pair of the no more than three ICG/ECG electrode pairs, a first ICG signal and a first heart electrical activity signal; sensing, with a first electrode contact and a second electrode contact of a second pair of the no more than three ICG/ECG electrode pairs, a second ICG signal and a second heart electrical activity signal; sensing, with a first electrode contact and a second electrode contact of a third pair of the no more than three ICG/ECG electrode pairs, a third ICG signal and a third heart electrical activity signal; utilizing a same clock to sense the first, second and third ICG signals and the first, second and third heart electrical activity signals; synchronizing in time the sensed first, second and third ICG signals with the first, second and third heart electrical activity signals; and determining a cardiac parameter based on the first, second and third ICG signals and an EKG signal based on the first, second and third heart electrical activity signals.

12. The method of claim 11, further comprising: employing the no more than three ICG/ECG electrode pairs to concurrently sense both ICG and heart electrical activity signals.

13. The method of claim 11, further comprising: employing the no more than three ICG/ECG electrode pairs to individually sense both ICG and heart electrical activity signals.

14. The method of claim 11, wherein at least one of the no more than three pairs of the three ICG/ECG electrode pairs includes first and second electrode contacts affixed to a substrate with a barrier disposed on the substrate between the first and second electrode contacts and protruding from the substrate, wherein the barrier is physically separated from the first and second electrode contacts by a sub-region of the substrate.

15. The method of claim 11, wherein the no more than three pairs of electrodes are based on the Wilson three-lead ECG configuration.

16. The method of claim 11, further comprising: processing the first, second and third ICG signals; and processing the first, second and third heart electrical activity signals.

17. The method of claim 11, further comprising: generating a biphasic ICG electrical current signal; and supplying the current signal to at least one of the contacts of the no more than three ICG/ECG electrode pairs.

18. The method of claim 17, wherein the biphasic ICG electrical current signal has a zero time-average value.

19. The method of claim 17, wherein the biphasic ICG electrical current signal has a polarization value equal to about a polarization of the electrodes.

20. The method of claim 11, wherein the no more than three ICG/ECG electrode pairs is exactly three ICG/ECG electrode pairs.

\* \* \* \* \*